United States Patent
Breitenbach et al.

(12)
(10) Patent No.: US 6,251,434 B1
(45) Date of Patent: Jun. 26, 2001

(54) PREPARATIONS OF NON-STEROIDAL ANALGESICS

(75) Inventors: Jörg Breitenbach, Mannheim; Joerg Rosenberg, Ellerstadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/101,694
(22) PCT Filed: Jan. 17, 1997
(86) PCT No.: PCT/EP97/00185
§ 371 Date: Jul. 15, 1998
§ 102(e) Date: Jul. 15, 1998
(87) PCT Pub. No.: WO97/26866
PCT Pub. Date: Jul. 31, 1997

(30) Foreign Application Priority Data

Jan. 23, 1996 (DE) ................................. 196 02 206

(51) Int. Cl.⁷ .............................. A61K 9/22; A61K 9/14; A61K 9/52; A61K 9/10
(52) U.S. Cl. .................. 424/486; 424/468; 424/457; 424/497
(58) Field of Search ..................... 424/484, 486, 424/468, 497, 457; 514/964, 961; 264/211.12

(56) References Cited

U.S. PATENT DOCUMENTS 4,801,460 * 1/1989 Goertz et al. .

FOREIGN PATENT DOCUMENTS

| 240 904 | 10/1987 | (EP) . |
| 607 467 | 7/1994 | (EP) . |
| 686 392 | 12/1995 | (EP) . |
| 96/29053 | 9/1996 | (WO) . |
| 96/29060 | 9/1996 | (WO) . |
| 96/29061 | 9/1996 | (WO) . |

OTHER PUBLICATIONS

Drug Invest 5 (4):238–242, 1993, Geisslinger et al.

* cited by examiner

Primary Examiner—Edward J. Webman
(74) Attorney, Agent, or Firm—Keil & Weinkauf

(57) ABSTRACT

Preparations of non-steroidal analgesics with antipyretic and antiinflammatory effect are obtainable by extrusion and shaping of a melt, comprising, besides one or more active ingredients, a mixture of a) 40–99.5% by weight of a homopolymer of N-vinylpyrrolidone with a Fikentscher K value of 30, b) 0.25–59.75% by weight of a water-soluble copolymer of N-vinylpyrrolidone, and c) 0.25–10% by weight of one or more physiologically acceptable salts of sodium or potassium, where the stated amounts are based on the total of components a), b) and c).

6 Claims, No Drawings

PREPARATIONS OF NON-STEROIDAL ANALGESICS

This is a 371 of International application No. PCT/EP97/00185, filed Jan. 17, 1997.

DESCRIPTION

The present invention relates to preparations of non-steroidal analgesics with antipyretic and antiinflammatory effect, obtainable by extrusion of a melt, comprising, besides one or more active ingredients, a mixture [lacuna]

a) 40–99.5% by weight of a homopolymer of N-vinylpyrrolidone with a Fikentscher K value of 30, b) 0.25–59.75% by weight of water-soluble N-vinyl [sic] copolymers, and c) 0.25–10% by weight of one or more physiologically acceptable salts of sodium or potassium, where the stated amounts are based on the total of components a), b) and c), and subsequent shaping.

The invention furthermore relates to a process for producing such preparations.

Rapid release of the active ingredient is crucially important particularly with analgesics in order to achieve a rapid onset of the pain-relieving effect.

In the case of active ingredients which have low solubility in water, like the organic acids which have analgesic activity, rapid release of adequate doses is often not simple to achieve (cf. Deutsche Apotheker Zeitung, No. 32, page 54).

EP-A 607 467 proposes promoting rapid release of ibuprofen by adding basic salts which are applied in the form of aqueous solutions during the pelleting process to the active ingredient which has been premixed with an ancillary substance. The pellets are subsequently compressed to tablets in a conventional way. This procedure is, however, relatively complicated and therefore economically unfavorable.

Recent investigations have shown that rapid release of ibuprofen can be achieved by using the corresponding lyrine [sic] salts (G. Geisslinger et al., Drug. Invest. SC4), 238–242, 1993).

It is furthermore known that drug forms can be produced in a very economic manner by extruding polymer melts which contain active ingredients, with subsequent continuous shaping.

EP-B 240 904 describes such a process for producing solid pharmaceutical forms by extruding polymer melts which contain active ingredients, the polymers used being homo- or copolymers of N-vinylpyrrolidone.

However, the basic problem in such a process is that the matrix-forming polymers on the one hand are sufficiently thermoplastic at the processing temperatures, or become processable by addition of a plasticizer, but on the other hand lead to drug forms which are stable under the usual storage conditions and with which no cold flow occurs.

This problem is all the more difficult to solve when the intention is to produce rapid release drug forms. Normally suitable for this purpose are, in particular, relatively low molecular weight polymers which rapidly dissolve in digestive fluids. However, it is precisely these which are prone to cold flow of the finished drug forms. High molecular weight polymers normally do not give rapid release and can scarcely be extruded without a plasticizer because the glass transition temperature (DIN 52324) is considerably higher.

An additional problem arises when transparent drug forms are to be produced by melt extrusion.

It is an object of the present invention to find transparent, rapid release preparations of non-steroidal analgesics which can be produced in a simple manner by melt extrusion with subsequent shaping and have a long shelf life.

We have found that this object is achieved by the preparations defined at the outset.

Suitable active ingredients according to the invention are non-steroidal analgesics with antipyretic and antiinflammatory effect, as also employed for symptomatic antirheumatic therapy.

Accordingly, suitable active ingredients are derivatives of salicyclic acid, such as acetylsalicylic acid, and derivatives of other organic acids and pyrazole derivatives and, where they exist, their physiologically tolerated salts. Thus, suitable active ingredients are aryl [sic] acid derivatives, such as diclofenac, tolmetin or zomepirac, also arylpropyl [sic] acid derivatives, such as ibuprofen, with both enantiomerically pure S(+)-ibuprofen and a racemate enriched with this enantiomer being embraced, as well as D,L-lysine salts of ibuprofen, naproxen, fenoprofen, flurbiprofen or ketoprofen, or else indole- and indeneacetic acid derivatives such as indomethacin or sulindac. Examples of suitable pyrazole derivatives are phenazone, amino-phenazone, metamizole, propyphenazone, phenylbutazone or oxy-phenbutazone.

Preferred active ingredients are ibuprofen, acetylsalicylic acid and ketoprofen, sulindac, indomethacin, flurbiprofen.

It is also possible to employ mixtures of active ingredients. Also suitable are mixtures of the analgesics with caffeine or codeine.

The preparations according to the invention comprise as component a) a homopolymer of N-vinylpyrrolidone with a Fikentscher K value of 30. This homopolymer is readily thermo- [sic] and water-solution, "water-soluble" meaning that at least 0.5 g, preferably at least 2 g, of the polymer dissolves, possibly as colloidal solution, in 100 g of water at 20° C. Preparation of the homopolymer is generally known.

Suitable as component b) are water-soluble copolymers of N-vinylpyrrolidone. Particularly suitable copolymers are those with vinyl acetate in amounts of 10–50%, particularly preferably those obtained by copolymerizing 60% by weight of N-vinylpyrrolidone and 40% by weight of vinyl acetate.

Suitable as component c) are physiologically tolerated sodium and/or potassium salts, also in the form of their hydrates, for example sodium acetate, potassium acetate, sodium carbonate, potassium carbonate, disodium [sic] bicarbonate, potassium hydroxide, sodium chloride or potassium chloride, sodium tricitrate [sic], with sodium acetate being preferred, particularly preferably as sodium acetate trihydrate.

The ratios of the amounts of components a), b) and c) are chosen according to the invention so that the preparations comprise a mixture of a) 40–99.5% by weight, preferably 45–95% by weight, of component a), b) 0.25–59.75% by weight, preferably 0.5–50% by weight, of component b), and c) 0.25–10% by weight, preferably 0.5–7% by weight, of component c), where the stated amounts are based on the total of a), b) and c).

Very particularly preferred drug forms comprise, besides the medicinal substance, a mixture of a) 60–85% by weight of component a)

b) 5–35% by weight of component b)

c) 0.5–5% by weight of component c).

The proportionate amount of the total of components a), b) and c) in the drug form is preferably from 60 to 85% by weight. Accordingly, the drug forms preferably comprise 15 to 40% by weight of one or more active ingredients.

The drug forms may additionally comprise 0 to 5% by weight of other conventional ancillary substances in the usual amounts.

The mixing of the active ingredient or ingredients with the polymeric binders and, where appropriate, pharmaceutical additives can take place before or after the melting of the polymeric binder by conventional processes. Mixing in an extruder is preferred, preferably a twin screw extruder or a single screw extruder with mixing compartment.

The melts contain no solvent. This means that no water and no organic solvent is added.

Production takes place by extrusion at from 50 to 180° C., preferably, 60 to 150° C. with subsequent shaping of the still plastic extrudate, eg. by shaping to tablets, for example as disclosed in EP-A 240 906 by passing the extrudate between two rolls which are driven in opposite directions and have mutually opposite depressions on the surface of the rolls, whose design determines the shape of the tablets. Cold cutting is also suitable.

A hot-cut process is preferred. This entails the extrudates being cut immediately after emerging from the die arrangement on the extruder by, for example, rotating knives or another suitable arrangement, expediently into pieces whose length is approximately equal to the diameter of the extrudate. The pellets which have been cut off cool in the stream of air or gas to such an extent that the surface is tack-free even before contact with other pellets or a vessel wall but, on the other hand, the pellets are still sufficiently plastic for them to acquire a spherical shape by collisions, eg. with the wall of a downstream cyclone. This results, in a simple manner, in substantially spherical or lenticular pellets with diameters of from 0.5 to 4, preferably 0.8 to 2 mm. The preferred smaller pellets are primarily suitable for packing capsules, but can also subsequently be compressed to tablets with the addition of other ancillary substances. The solid drug forms can also be provided with a conventional coating to improve the appearance and/or the taste (sugar-coated tablet).

The preparations according to the invention of non-steroidal analgesics with antipyretic and antiinflammatory effect are transparent, stable on storage and show rapid release. "Rapid release" means that the release of the active ingredient is at least 70% after 30 min, measured by the USP XXII paddle method.

Surprisingly, despite use of a relatively high molecular weight polymer, even drug forms weighing as much as 1000 mg show rapid release. The advantage of large tablets is that they can also be used as pastilles without being swallowed. Elderly patients or patients with dysphagia often find difficulty in swallowing larger tablets so that rapid release pastilles have great advantages.

It is surprising that it is possible to find a mixture of components a and b for every size of the form (1000, 850 or 650 mg bolus) which achieves a maximum release which is distinctly greater than the release from mixtures of different composition, or especially of the individual polymers alone.

The release rate also exceeds that of solid solutions produced by a solvent process as described in the literature (M. Najib, M. Suleilman, A. Malakh, 32 (1986) 229–236.)

EXAMPLES

The compositions indicated in each of the examples were premixed and introduced into the feed section of a twin screw extruder (Werner & Pfleiderer, ZSK 30). The melt extrusion took place with a product throughput of 3 to 4 kg/h. The temperatures in the individual zones (sections) of the extruder, and the temperature of the heated die strip, are indicated for each of the tests. Tablets weighing 1000, 850 or 650 mg were produced from the extrudate by the calendering process described in EP-B 240 906.

| Extrusion conditions: | |
|---|---|
| Section 1: | 43° C. |
| Section 2: | 57° C. |
| Section 3: | 120° C. |
| Section 4: | 100° C. |
| Section 5: | 100° C. |
| Head: | 100° C. |
| Die: | 100° C. |
| Calender temperature: | 18° C. |

The release of active ingredient was measured by the USP XXII paddle method. This in vitro test method is used to determine the rate of dissolution of articles, eg. tablets, containing active ingredients. For this purpose 900 ml of a phosphate buffer with a pH of 7.2 were equilibrated at 37° C. in a 1 l round-bottom vessel. An appropriate amount of drug form was weighed in. The release of active ingredient from the tablets was determined in this USP XXII no-change test by UV spectroscopy after 30 min in each case with a paddle speed of 150 rpm.

Example 1

| Tablet weight 850 mg | |
|---|---|
| Composition: | |
| Ibuprofen | 26.0% by weight |
| Kollidon ® K 30[1] | 56.5% by weight |
| Kollidon ® VA 64[2] | 15.0% by weight |
| Na acetate × 3 H$_2$O | 2.0% by weight |
| Fine-particle silica | 0.5% by weight |
| Release after 30 min. | 88.0% by weight |

[1] PVP homopolymer, Fikentscher K value 30
[2] Copolymer, obtained from 60% by weight of N-vinylpyrrolidone and 40% by weight of vinyl acetate, K value 30.

Example 2

| Tablet weight 650 mg | |
|---|---|
| Composition: | |
| Ibuprofen | 33.0% by weight |
| Kollidon ® K 30 | 44.2% by weight |
| Kollidon ® VA 64 | 20.0% by weight |
| Na acetate × 3 H$_2$O | 2.0% by weight |
| Fine-particle silica | 0.8% by weight |
| Release after 30 min: | 90.0% by weight |

Example 3

| Tablet weight 850 mg | |
|---|---|
| Composition: | |
| Ibuprofen | 23.5% by weight |
| Kollidon ® K 30 | 59.0% by weight |

-continued

| Tablet weight 850 mg | |
|---|---|
| Kollidon ® VA 64 | 15.0% by weight |
| Na acetate × 3 H$_2$O | 2.0% by weight |
| Fine-particle silica | 0.5% by weight |

The bioavailability in dogs was determined:
6 dogs, single administration of 1 table per animal
Crossover study with 1-week washout.

The active ingredient contents in the plasma were determined by HPLC with UV-detection.

For comparison, a commercial product containing 342 mg of ibuprofen D,L-lysinate (equivalent to 200 mg of ibuprofen) was administered under the same conditions.

The results are listed in the table.

TABLE

Pharmacokinetics in dogs

| | Plasma level [μg/ml] × 10$^3$ | |
|---|---|---|
| Time [h] | Tablet of Ex. 3 | Ibuprofen lysinate |
| 0.25 | 14.98 | 6.37 |
| 0.5 | 35.12 | 13.45 |
| 0.75 | 42.19 | 25.83 |
| 1.0 | 51.06 | 35.27 |
| 1.5 | 55.16 | 46.07 |
| 2.0 | 49.13 | 47.82 |
| 2.5 | 43.23 | 40.65 |
| 3.0 | 38.12 | 39.66 |
| 4.0 | 34.63 | 32.42 |
| 6.0 | 23..49 | 35.72 |
| 8.0 | 14.40 | 14.46 |
| 24.0 | 0.71 | 0.90 |

We claim:

1. A pharmaceutical composition obtained by extrusion and shaping of a melt, comprising, a mixture of a) a non-steroidal analgesic with antipyretic and antiinflammatory effects b) 40–99.5% by weight of a homopolymer of N-vinylpyrrolidone with a Fikentscher K value of 30, c) 0.25–59.75% by weight of a water-soluble copolymer of N-vinylpyrrolidone, and d) 0.25–10% by weight of one or more physiologically acceptable salts of sodium or potassium, where the stated amounts are based on the total of components b), c) and d).

2. The composition of claim 1, comprising 15–40% by weight of one or more of said analgesic ingredients and 60–85% by weight of a mixture of components b), c) and d).

3. The composition of claim 1, comprising a component c) which is obtained by copolymerization of 60% by weight of N-vinylpyrrolidone and 40% by weight of vinyl acetate.

4. The composition of claim 1, comprising sodium acetate as component d.

5. The composition of claim 1, comprising ibuprofen as analgesic.

6. A process for producing the composition of claim 1 which process comprises extruding a melt comprising one or more of said analgesics and a mixture of b) 40–99.5% by weight of a homopolymer of N-vinylpyrrolidone with a Fikentscher K value of 30, c) 0.25–59.75% by weight of a water-soluble copolymer of N-vinylpyrrolidone, and d) 0.25–10% by weight of one or more physiologically acceptable salts of sodium or potassium, where the stated amounts are based on the total of components b), c) and d), and shaping the melt while still plastic.

* * * * *